United States Patent [19]

Horne et al.

[11] Patent Number: 4,922,754
[45] Date of Patent: May 8, 1990

[54] ACOUSTIC EMISSION TRANSDUCER AND MOUNTING ADAPTER FOR MONITORING METALCUTTING TOOLS

[75] Inventors: John G. Horne, Lafayette; David A. Dornfeld; Keith A. McMillen, both of Berkeley, all of Calif.

[73] Assignee: Kennametal Inc., Latrobe, Pa.

[21] Appl. No.: 395,193

[22] Filed: Aug. 15, 1989

Related U.S. Application Data

[63] Continuation of Ser. No. 324,959, Mar. 17, 1989, abandoned, which is a continuation of Ser. No. 944,556, Dec. 19, 1986, abandoned.

[51] Int. Cl.⁵ .......................................... G01N 29/00
[52] U.S. Cl. ........................................ 73/587; 73/644
[58] Field of Search .................. 73/587, 644, 660, 632, 73/866.5; 340/683, 680; 310/334, 336

[56] References Cited

U.S. PATENT DOCUMENTS

| | | | |
|---|---|---|---|
| 3,545,262 | 12/1970 | Steele et al. | 73/514 |
| 3,713,127 | 1/1973 | Keledy et al. | 340/540 |
| 3,782,183 | 1/1974 | O'Connor et al. | 73/100 |
| 3,935,484 | 1/1976 | Leschek et al. | 310/346 |
| 4,011,472 | 3/1977 | Feng | 73/587 |
| 4,129,042 | 12/1978 | Rosvold | 73/727 |
| 4,138,898 | 2/1979 | Dybel | 73/767 |
| 4,189,655 | 2/1980 | Bruel | 310/329 |
| 4,478,538 | 10/1984 | Kakino | 73/104 |
| 4,549,437 | 10/1985 | Weins et al. | 73/587 |
| 4,563,897 | 1/1986 | Moore | 73/587 |
| 4,574,633 | 3/1986 | Ohnuki et al. | 73/587 |
| 4,656,868 | 4/1987 | Azuma et al. | 340/680 |

FOREIGN PATENT DOCUMENTS

53-131080 4/1977 Japan.
896547 6/1978 U.S.S.R..

OTHER PUBLICATIONS

Perry, R. H. et al. "Chemical Engineer's Handbook" Fifth Ed. (1973).

*Primary Examiner*—Hezron E. Williams
*Assistant Examiner*—Louis M. Arana
*Attorney, Agent, or Firm*—Stephen T. Belsheim

[57] ABSTRACT

An acoustic emission transducer has an improved design and mounting arrangements for using it to monitor machine tool operating condition. The transducer has a hollow housing with external threads capable of making a threaded mounting connection through which acoustic emission energy generated by operation of a machine tool propagates and is then transmitted by the housing. Also, a wear plate is attached to one end of the externally-threaded housing and supports a piezoelectric detecting element in the housing. The plate is capable of transmitting acoustic emission energy and the detecting element is capable of detecting it and generating an electrical signal in response thereto. In a surface mounting arrangement of the transducer, an adapter is used in mounting the transducer to a surface of the machine tool support structure. In an integral mounting arrangement of the transducer, the housing of the transducer is threaded directly into an internally threaded cavity in the machine tool support structure. In both mounting arrangements, a contact ball is disposed in a recess formed in the machine tool support structure below the transducer plate for providing acoustic emission energy transmitting contact between the transducer plate and the machine tool support structure.

17 Claims, 2 Drawing Sheets

ACOUSTIC EMISSION TRANSDUCER AND MOUNTING ADAPTER FOR MONITORING METALCUTTING TOOLS

This is a continuation of copending application Ser. No. 07/324,959 filed on Mar. 17, 1989, now abandoned, which is a continuation of co-pending application Ser. No. 06/944,556 filed on Dec. 19, 1986, now abandoned.

BACKGROUND OF THE INVENTION

The present invention generally relates to monitoring the condition of machine tools by acoustic emission detection and, more particularly, is concerned with improvements in the design of acoustic emission transducers and in the mounting thereof to the support structures of machine tools, such as used in metalcutting processes.

Materials under stress, experiencing fracture and cracking, are known to produce wave-like bursts of strain energy, commonly referred to as stress wave or acoustic emission. This phenomenon has been employed heretofore to monitor the operating conditions of machine tools, such as lathes, drilling machines, metalcutting tools and the like, to detect tool deterioration and damage, for instance, due to crack growth. Representative patents related to detection of acoustic emission for monitoring tool condition during operation are the devices, disclosed in U.S. Patents to Keledy et al, (U.S. Pat. No. 3,713,127), Feng (U.S. Pat. No. 4,011,472), Moore (U.S. Pat. No. 4,563,897) and Ohnuki et al (U.S. Pat. No. 4,574,633).

However, commercially-available acoustic emission transducers have mostly been developed for well-established acoustic emission monitoring applications, such as defect detection. These transducers are not designed ideally for detecting the acoustic emission signals encountered in machining, nor designed appropriately for installation in association with a machine tool. For instance, one presently-available transducer has a smooth-surfaced cylindrical configuration and is placed in a pocket machined out of the supporting structure, such as the shank, of the machine tool. A couplant is used with a compliant element to keep the transducer against the wall of the pocket. Although this particular transducer functions reasonably well in practice, it has several limitations which adversely impact its performance and versatility. The principal limitations include: first, the necessity of hand fitting the transducer during assembly to ensure uniform transducer mounting from machine tool to machine tool; second, the difficulty of putting strain relief on the cable of the transducer; and, third, the necessity to adopt several different installation methods depending on the machine tool being instrumented.

Consequently, a need exists for improvements in the design and mounting of acoustic emission transducers which will overcome these deficiencies and facilitate their application in the machine tool environment.

SUMMARY OF THE INVENTION

The present invention provides improvements in acoustic emission transducers designed to satisfy the aforementioned needs. The present invention encompasses several different improvements which substantially overcome the limitations exemplified in the one above-described presently-available transducer and yield rugged, versatile and cost-effective acoustic emission transducer mounting arrangements, especially adapted to the rigorous machine tool environment such as found, for example, in metalcutting. The improvements relate to acoustic emission transducer design and integral and surface types of acoustic emission transducer mounting arrangements which can be associated together with the same machine tool; however, the advantages to be derived from each of these different improvements also can be enjoyed separately from one another in association with different machine tools.

Accordingly, the present invention relates to improvements in acoustic emission transducer design adapting the transducer for use in monitoring machine tool operating condition. Such improved acoustic emission transducer includes a hollow housing having external threads capable of receiving and transmitting acoustic emission energy generated by operation of a machine tool and impinging on its external threads, and an acoustic emission energy detecting means attached to the housing and being capable of receiving and detecting acoustic emission energy transmitted by the housing and generating an electrical signal in response to detection of the energy.

More particularly, the acoustic energy detecting means includes a plate attached to the housing and being capable of transmitting acoustic emission energy impinging thereon, and an acoustic emission energy detecting element attached to the plate and being disposed within the housing in a spaced relation thereto by the plate. The element, preferably composed of material exhibiting piezoelectric properties, is capable of detecting acoustic emission energy impinging upon and transmitted by the plate and of generating the electrical signal in response to detection of the energy. The transducer housing is defined by a tubular sleeve having the external threads defined circumferentially thereon, a central bore and a pair of open opposite ends. The plate is a ceramic wear plate attached to the sleeve at one of its opposite open ends. The transducer also has an electrical signal transmission means mounted to the housing and electrically connected to the detecting element. Specifically, the signal transmission means is a cable and a strain relief cap mounting the cable to the sleeve at one of its opposite open ends, with the cable being electrically connected to the detecting element.

In addition, the present invention relates to improvements facilitating surface mounting of the transducer to a machine tool support structure. Specifically, a surface-mountable adapter is provided with has an annular-shaped body with an internally-threaded central bore adapted to threadably receive the externally-threaded acoustic emission transducer, an annular-shaped flange integrally connected to and extending radially outwardly from the body, and means defined in the flange for facilitating attachment of the adapter to the machine tool support structure. More particularly, the means facilitating attachment are a series of holes defined in the flange. Also, the body and flange together define a surface at one end of the adapter configured to be placed in flush contact with a surface on a machine tool support structure.

The present invention also relates to improvements incorporated in the surface type of acoustic emission transducer mounting arrangement. The mounting arrangement includes the externally-threaded acoustic emission transducer, and the surface mountable internally-threaded adapter adapted to receive the externally-threaded transducer and form a threaded connection therewith. The adapter is adapted to be mounted to a surface of a machine tool support structure for receiving acoustic emission energy therefrom and transmitting the same through the threaded connection to the transducer for monitoring machine tool operating condition. The arrangement also includes a contact ball disposable in a recess formed in the machine tool support structure for providing acoustic emission energy transmitting contact between the transducer and the machine tool support structure when the adapter is mounted to the machine tool support structure surface so as to position the transducer in overlying relation to the recess.

Finally, the present invention relates to improvements incorporated in the integral type of acoustic emission transducer mounting arrangement. The integral mounting arrangement includes the externally-threaded acoustic emission transducer, and a machine tool support structure having an internally-threaded cavity formed therein adapted to receive the externally-threaded transducer and form a releasably threaded connection therewith. The threaded connection is capable of transmitting acoustic emission energy generated by operation of a machine tool and impinging on the threaded connection to the transducer for monitoring machine tool operation. Also, the mounting arrangement includes a contact ball disposed below the transducer in a recess formed in the machine tool support structure below the threaded cavity for providing acoustic emission energy transmitting contact between the transducer and machine tool support structure.

These and other advantages and attainments of the present invention will become apparent to those skilled in the art upon a reading of the following detailed description when taken in conjunction with the drawings wherein there is shown and described illustrative embodiments of the invention.

BRIEF DESCRIPTION OF THE DRAWINGS

In the course of the following detailed description, reference will be made to the attached drawings in which.

DETAILED DESCRIPTION OF A SPECIFIC EMBODIMENT

Figure 1:
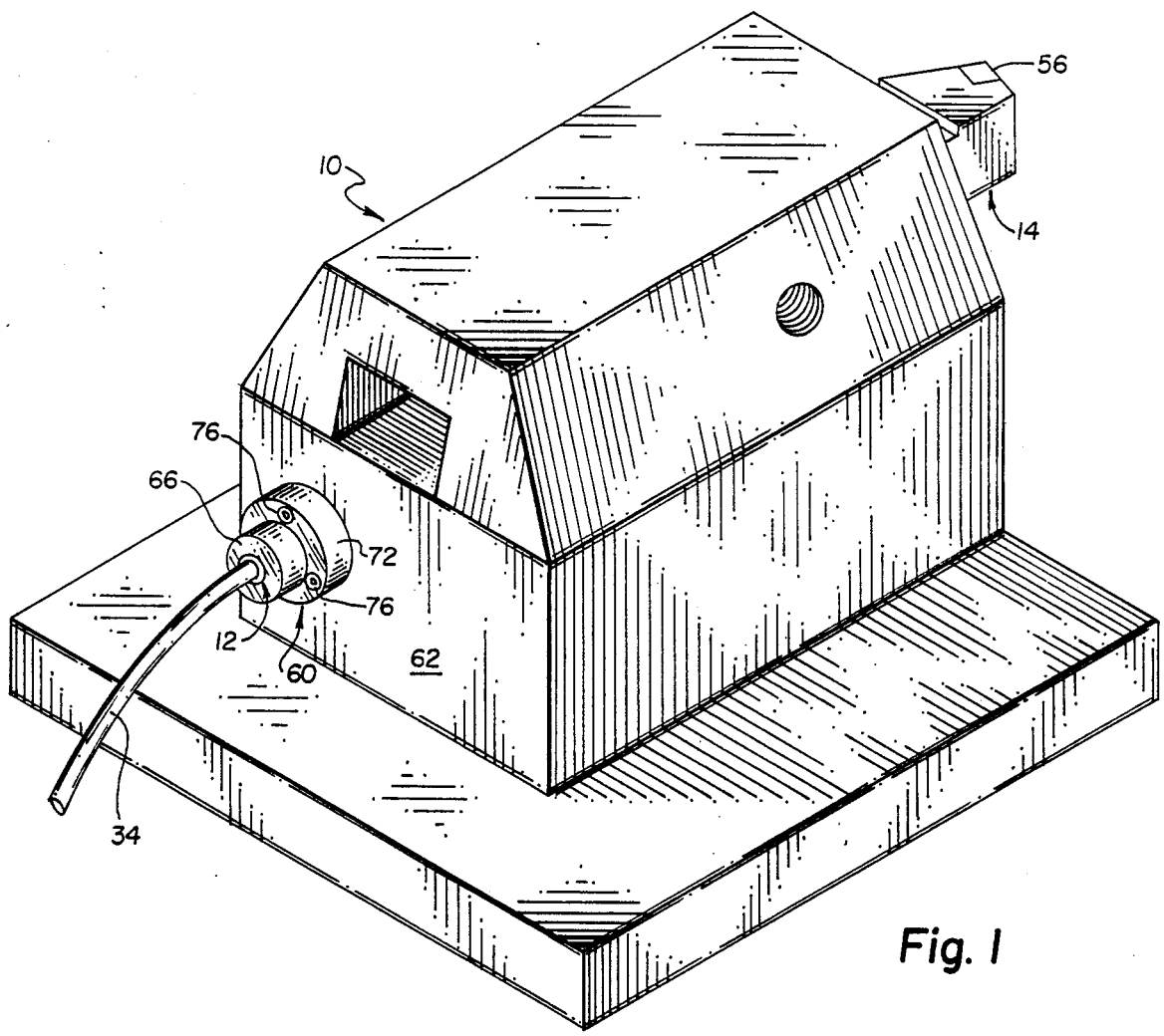
FIG. 1 is a perspective view of a machine tool block supporting a metalcutting tool and incorporating both the integral and surface types of acoustic emission transducer mounting arrangements which embody the improvements of the present invention.
Figure 2:
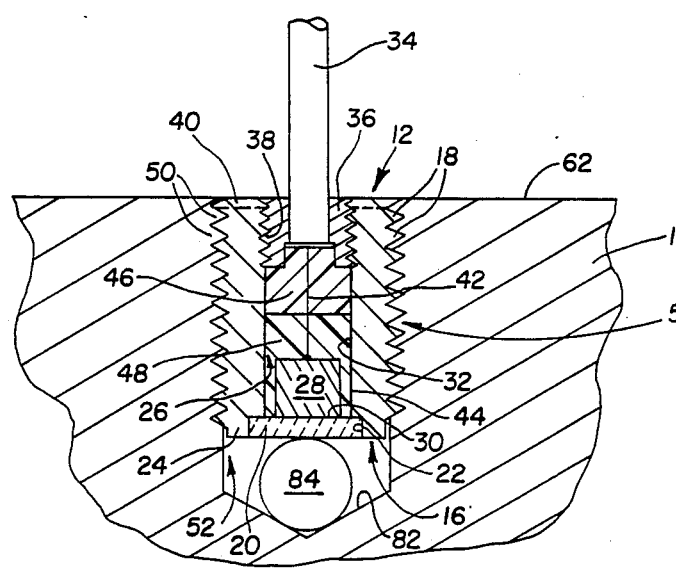
FIG. 2 is an enlarged fragmentary sectional view of the machine tool block of FIG. 1, illustrating the integral type of acoustic emission transducer mounting arrangement.
Figure 3:
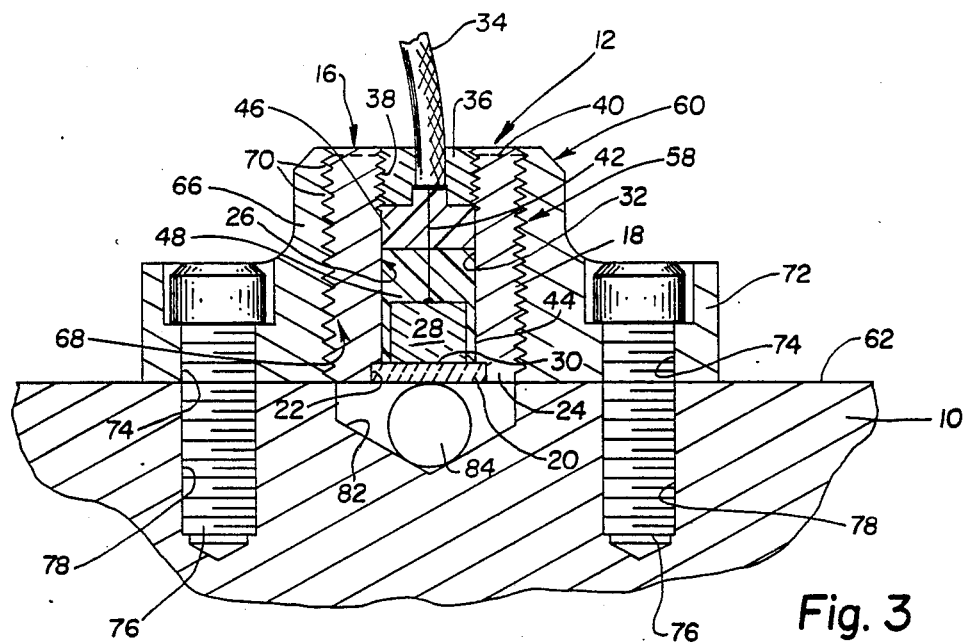
FIG. 3 is another enlarged fragmentary sectional view of the machine tool block of FIG. 1, illustrating the surface type of acoustic emission transducer mounting arrangement.

Referring now to the drawings, and particularly to FIG. 1, there is shown a machine tool support structure in the form of a machine tool block, generally designated by the numeral 10, with which are associated the improvements of the present invention. The improvements concern the design of an acoustic emission transducer, generally indicated as 12, and the mounting thereof either integrally with the machine tool support structure 10, as seen in FIG. 2, or on the surface of the support structure 10, as shown in FIG. 3. In either mounting arrangement, the transducer 12 is located sufficiently near to a machine tool 14, such as a metalcutting tool, to be able to monitor its operating condition.

The acoustic emission transducer 12 has a hollow housing 16 in the form of a metal sleeve with external circumferential threads 18 capable of making a releasable threaded mounting connection, in either type of mounting arrangement as will be explained below. Acoustic emission energy generated by operation of the machine tool 14 propagates within the machine tool support structure 10 and through the threaded mounting connection and then is transmitted by the housing 16.

The transducer 12 further includes means in the form of a plate 20, such as a ceramic wear plate, being attached, such as by bonding using a suitable epoxy, within a circular recess 22 in the housing 16 defined across its lower end 24. At such location, the wear plate 20 closes and seals a lower open end of a central bore 26 defined through the housing 16. A detecting element 28 is mounted, such as by bonding with a suitable adhesive, on the inner surface 30 of the wear plate 20 which faces toward the bore 26. The detecting element 28, being composed of a material which exhibits piezoelectric properties, thus extends above the wear plate 20 and within the central bore 26 of the housing 16. In particular, the detecting element 28 is spaced inwardly from a circumferential interior surface 32 of the housing 16 which defines the bore 26. The wear plate 20 which directly connects with the detecting element 28 is capable of transmitting acoustic emission energy from the housing 16 to the detecting element 28 which, in turn, is capable of detecting it and generating an electrical signal in response thereto.

Also, the transducer 12 includes electrical signal transmission means in the form of an electrical cable 34, such as an armored signal cable, and an externally-threaded strain relief cap 36. The cap 36 is releasably threaded into an internally-threaded upper portion 38 of the interior surface 32 of the housing 16 so as to close and seal an upper open end of the bore 26 and mount the cable 34 to the housing at its upper end 40. The cable 34 includes an electrical conductor 42 which extends axially through the bore 26 and is electrically connected, such as by solder, to the upper end of the detecting element 28. The lower end of the detecting element 28 is grounded by another electrical conductor 44 which is connected between the element 28 and the housing 16. The detecting element 28 does not make direct mechanical contact with the housing 16 so as to avoid electrical contact therewith which would short-circuit the element. Instead, the detecting element 28 is connected indirectly thereto by the wear plate 20 which also serves to electrically insulate the detecting element 28 from the housing. The space within the bore 26 between the cap 36 and detecting element 28 and surrounding the latter in the gap between it and the housing 16 is filled at the upper half of the space by a suitable epoxy 46 and the lower half by a suitable adhesive 48.

In an exemplary embodiment of the transducer 12, it is nominally $\frac{3}{8}$ inch in diameter and $\frac{3}{4}$ inch in length. The epoxy 46 is a two-part epoxy available from Dow Chemical and the adhesive 48 is a two-part RTV self-leveling adhesive. The detecting element 28 is a 0.250 inch diameter by 0.162 inch thick PZT piezocrystal available from Channel Industries, designated as C5500, being bonded to the wear plate 20 with cyanoacrylate adhesive. The wear plate 20 is a 0.375 inch diameter by 0.0625 inch thick Alumina 94 ceramic wear plate bonded into the recess 22 of the housing with the Dow Chemical two-part epoxy. The conductors 42, 44 are 28-gauge signal and ground wires attached with 60/40 solder.

Figure 4:
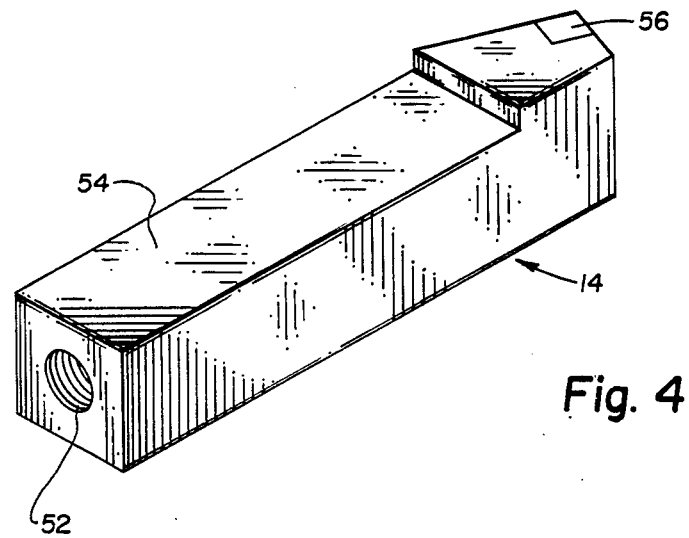
FIG. 4 is an enlarged perspective view of the metalcutting tool removed from the tool block of FIG. 1, illustrating a threaded bore in one end thereof adapted to integrally mount the acoustic emission transducer therein in accordance with the integral type of transducer mounting arrangement.

In the integral acoustic emission detection mounting arrangement of the transducer 12 as seen in FIG. 2, the external circumferential threads 18 on the housing 16 of the transducer 12 are threaded directly into internal threads 50 of a cavity 52 tapped in the machine tool support structure 10. The cavity 52 is shown in FIG. 1 without the transducer 12 being present. Also, the cavity 52 can be seen in FIG. 4 tapped in a support structure which is the shank 54 of the machine tool 14 itself, being located at an end of the shank opposite the tool head 56. The releasable threaded mounting connection, generally designated 58, formed by the external and internal threads 18, 50 greatly increases the area of surface contact between the transducer housing 16 and the machine tool support surface 10 so as to transmit to the detecting element 28 within the housing 16 more of the acoustic emission energy generated by operation of the machine tool 14, which propagates through the support structure 10 and impinges on the threaded connection 58 of the transducer 12. As a result, more sensitive monitoring of machine tool operation is accomplished. In addition, the sensitivity of the transducer 12 is enhanced by use of a lubricant on its external threads 18. An ordinary bench grease has been found to be suitable for this purpose.

In a surface acoustic emission detection mounting arrangement of the transducer 12 as seen generally in FIG. 1 and in detail in FIG. 3, an internally-threaded surface-mountable adapter 60 is used in mounting the transducer 12 to a surface 62 of the machine tool support structure 10. This mounting arrangement is most advantageously used where the portion of the support structure 10 being available for use in monitoring the machine tool 14 is not of a thickness sufficient to incorporate the integral mounting of the transducer 12 therein. Thus, the surface-mountable adapter 60 is capable of receiving the externally-threaded transducer 12 and forming a releasable threaded mounting connection 64 therewith, and also, in turn, is capable of being mounted to the surface 62 of the machine tool support structure 10 for receiving acoustic emission energy therefrom and transmitting the same through the threaded connection 64 to the transducer 12 for monitoring the operating condition of the machine tool 14.

More particularly, the surface-mountable adapter 60 includes an annular-shaped body 66 having a central bore 68 with internal circumferential threads 70 adapted to threadably receive and form the releasable threaded mounting connection 64 with the external threads 18 on the acoustic emission transducer housing 16. In addition, the adapter 60 has an annular-shaped flange 72 integrally connected to and extending radially outwardly from the body 66 along approximately one-half of its axial extend from one of its end. Means in the form of a plurality of circumferentially spaced holes 74 are defined in the flange 72 for facilitating attachment of the adapter 60 to the surface 62 of the machine tool support structure 10 by a series of bolts 76 which fit through the flange holes 74 and are then threaded into complementarily threaded holes 78 tapped into the support structure 10. At their lower ends, the adapter body 66 and flange 72 together define a surface 80, being planar in the illustrated embodiment, adapted to form a flush contact with the surface 62 on the support structure 10. As before, to improve sensitivity of the transducer 12, a lubricant can be used at the threaded connection 64 and at the surface 80.

Compared to the integral mounting arrangement wherein the upper end 40 of the transducer housing 16 is disposed at the level of the support structure surface 62 with the transducer within the cavity 52 below the surface, in the surface mounting arrangement the transducer 12 is located above the surface 62 and its wear plate 20 and housing lower end 24 overlie a recess 82 formed in the support structure 10. In the integral mounting arrangement, such recess 82 is also present but located below or at the bottom of the internally-threaded cavity 52. In both mounting arrangements, preferably, a contact ball 84 is disposed in the recess 82 for providing acoustic emission energy transmitting contact between the transducer wear plate 20 and the machine tool support structure 10. This contact is primarily a point-to-point contact as opposed to a potentially non-uniform surface-to-surface contact made at the threaded connections of the housing 16. It has been found that sufficient acoustic emission energy propagates through the threads that use of the contact ball 84 can be considered as optional.

In both mounting arrangements, whether it be in the integral mounting arrangement or in the surface mounting arrangement, the transducer is installed to a predetermined torque limit. Consequently, no special hole preparation is required except for drilling and tapping the hole.

It is readily apparent that the improved design of the acoustic emission transducer 12 provides a threaded package which is simple to mount in a variety of places on the machine tool support structure 10. Also, the threaded package is sealed which eliminates the need to take special precautions to prevent contamination.

Another advantage of the invention is that the transducer can be precalibrated so that no field calibration is required during installation, except that the transducer must be installed to a preset torque and that sufficient signal level is verified. Further, it should be appreciated that the invention can accommodate a variety of piezoelectric elements or additional piezoelectric elements if changes in tool performance are desired, for example, for rotating tool work.

The improvements of the present invention and the attendant advantages will be understood from the foregoing description and it will be apparent that various changes may be made in the form, construction and arrangement of the parts thereof without departing from the spirit and scope of the invention or sacrificing all of its material advantages, the forms hereinbefore described being merely preferred or exemplary embodiments thereof.

What is claimed is:

1. A surface-mountable acoustic emission detection arrangement for use in monitoring the operating condition, of a machine tool said arrangement comprising:

an externally-threaded acoustic emission transducer;

a surface-mountable internally-threaded adapter for receiving said externally-threaded transducer and forming a releasable threaded connection therewith, said adapter being mountable to a surface of a machine tool support structure for receiving acoustic emission energy therefrom and transmitting the same through said threaded connection to said transducer for monitoring machine tool operating condition; and a contact ball disposable in a recess formed in the machine tool support structure surface for providing acoustic emission energy transmitting contact between said transducer and the machine tool support structure when said adapter is mounted to the machine tool support structure surface so as to position said transducer in overlying relation to the recess.

2. The detection arrangement as recited in claim 1, wherein said transducer includes:

a hollow housing having external threads, said housing receiving and transmitting acoustic emission energy impinging on said external threads; and acoustic emission energy detecting means, attached to said housing, for receiving and detecting acoustic emission energy transmitted by said housing and generating an electrical signal in response to detection of said energy.

3. The transducer as recited in claim 2 wherein said acoustic energy detecting means includes:

a plate attached to said housing and being capable of transmitting acoustic emission energy impinging thereon; and an acoustic emission energy detecting element attached to said plate and being disposed within said housing in a spaced relation thereto by said plate, said element being capable of detecting acoustic emission energy impinging upon and transmitted by said plate and of generating said electrical signal in response to detection of said energy.

4. The transducer as recited in claim 3 wherein said detecting element is composed of a material which exhibits piezoelectric properties.

5. The transducer as recited in claim 3 further comprising an electrical signal transmission means mounted to said housing and electrically connected to said detecting element.

6. The transducer as recited in claim 3 wherein said housing is defined by a tubular sleeve having said external threads defined circumferentially thereon, a central bore and a pair of open opposite ends.

7. The transducer as recited in claim 6 further comprising an electrical signal transmission means mounted to said housing and electrically connected to said detecting element.

8. The transducer as recited in claim 7 wherein said signal transmission means is a cable and a strain relief cap mounting said cable to said sleeve at one of its opposite open ends.

9. An integral acoustic emission detection arrangement for use in monitoring the operating condition of a machine tool, said arrangement comprising:

an externally-threaded acoustic emission transducer;

a machine tool support structure having an internally-threaded cavity formed therein to receive said externally threaded transducer and to form a releasable threaded connection therewith, said threaded connection transmitting acoustic emission energy generated by operation of a machine tool and impinging on said threaded connection to said transducer for monitoring machine tool operation; and a contact ball disposed below said transducer in a recess formed in said machine tool support structure below said cavity for providing acoustic emission energy transmitting contact between said transducer and machine tool support structure.

10. The detection arrangement as recited in claim 9 wherein said acoustic emission transducer includes a hollow housing having external threads, said housing receiving and transmitting acoustic emission energy impinging on said external threads, and an acoustic emission energy detection means, attached to said housing, for receiving and detecting acoustic emission energy transmitted by the housing and generating an electrical signal in response to detection of said energy.

11. The transducer as recited in claim 10 wherein said acoustic energy detecting means includes:

a plate attached to said housing and being capable of transmitting acoustic emission energy impinging thereon; and an acoustic emission energy detecting element, attached to said plate and being disposed within said housing in a spaced relation thereto by said plate, for detecting acoustic emission energy impinging upon and transmitted by said plate and of generating said electrical signal in response to detection of said energy.

12. The transducer as recited in claim 11 wherein said detecting element is composed of a material which exhibits piezoelectric properties.

13. The transducer as recited in claim 11 further comprising an electrical signal transmission means mounted to said housing and electrically connected to said detecting element.

14. The transducer as recited in claim 11 wherein said housing is defined by a tubular sleeve having said external threads defined circumferentially thereon, a central bore and a pair of open opposite ends.

15. The transducer as recited in claim 14 further comprising an electrical signal transmission means mounted to said housing and electrically connected to said detecting element.

16. The transducer as recited in claim 15 wherein said signal transmission means is a cable and a strain relief cap mounting said cable to said sleeve at one of its opposite open ends.

17. An integral acoustic emission detection arrangement for use in monitoring the operating condition of a machine tool, said arrangement comprising;

an externally-threaded acoustic emission transducer; and a machine tool support structure having an internally-threaded cavity formed therein adapted to receive said externally threaded transducer and form a releasable threaded connection therewith, said threaded connection transmitting acoustic emission energy generated by operation of a machine tool and impinging on said threaded connection to said transducer for monitoring machine tool operation, wherein said transducer includes:

a hollow housing having external threads for receiving and transmitting acoustic emission energy impinging on said external threads, acoustic emission energy detecting means attached to said housing for receiving and detecting acoustic emission energy transmitted by said housing and generating an electrical signal in response to detection of said energy, wherein said acoustic energy detecting means includes a plate attached to said housing and disposed in overlying relation to said recess defined in said machine tool support, and a contact ball disposed below said transducer plate in a recess formed in said machine tool support structure below said cavity for providing acoustic emission energy transmitting contact between said transducer plate and machine tool support structure.

* * * * *

UNITED STATES PATENT AND TRADEMARK OFFICE
CERTIFICATE OF CORRECTION

PATENT NO. : 4,922,754

DATED : May 8, 1990

INVENTOR(S) : Horne et al.

It is certified that error appears in the above-identified patent and that said Letters Patent is hereby corrected as shown below:

ON TITLE PAGE:

At [75] add -- Ted R. Massa, Latrobe, Pennsylvania --

Signed and Sealed this

Twenty-third Day of June, 1992

Attest:

DOUGLAS B. COMER

*Attesting Officer*     Acting Commissioner of Patents and Trademarks